United States Patent [19]
Kessler

[11] Patent Number: 5,921,947
[45] Date of Patent: Jul. 13, 1999

[54] BANDAGE FOR THE FIXATION OF THE ANKLE JOINT

[76] Inventor: Sigurd Kessler, Am Mühlanger 70, Puchheim, Germany, 82178

[21] Appl. No.: 08/910,870

[22] Filed: Aug. 13, 1997

[30] Foreign Application Priority Data

Aug. 14, 1996 [DE] Germany .............................. 296 14 127
Jul. 9, 1997 [EP] European Pat. Off. ............... 97111664

[51] Int. Cl.⁶ ....................................................... A61F 5/00
[52] U.S. Cl. ............................................... 602/27; 602/65
[58] Field of Search ................................ 602/5, 27, 28, 602/65, 66

[56] References Cited

FOREIGN PATENT DOCUMENTS

| 9211750 U | 4/1993 | Germany . |
| 4301145A1 | 7/1994 | Germany . |
| 8602369 | 4/1988 | Netherlands . |
| 8700578 | 10/1988 | Netherlands . |
| WO 82/01659 | 5/1982 | WIPO . |

*Primary Examiner*—Linda C.M. Dvorak
*Attorney, Agent, or Firm*—Townsend and Townsend and Crew LLP

[57] ABSTRACT

The invention relates to a bandage for the fixation of an ankle joint of an ankle of a foot. The bandage comprises a ring element arranged in an area of a lateral malleolus. At least one tension strap is provided at an outer side of the foot and connected with the ring element in the area of the lateral malleolus. The tension strap extends from the ring element to at least one free tension strap end substantially in a direction of a middle foot or a forefoot of the foot. The free tension strap end includes a fastener section for fastening to a coupling surface of a part fixed relative to the foot. A ring bandage surrounds a malleolar region of the ankle, and has first and second ends extending substantially in the direction of the lateral malleolus and connected with the ring element. The ring bandage has a length which is adjustable for tensioning the tension strap.

26 Claims, 3 Drawing Sheets

BANDAGE FOR THE FIXATION OF THE ANKLE JOINT

FIELD OF THE INVENTION

The present invention relates to a bandage for the fixation of the ankle joint, comprising at least one tension strap provided at the outer side of the foot and extending substantially in the direction of the lateral malleolus and capable of being tensioned by means of a ring bandage which surrounds the malleolar region and engages the respective tension strap.

DESCRIPTION OF PRIOR ART

Injuries to ligaments in the area of the ankle joint occur very frequently in practice and are, as a rule, a consequence of the twisting of the ankle. This frequently leads to stretching, rupture or tearing of ligaments, which are very painful. The ligament which extends in the direction of the forefoot between the fibula and the talus is particularly frequently affected.

In order to enable the injury to heal and to counteract the pain which arises, the ankle joint is kept still by applying a plaster, by bandaging it to an L-rail or splint or by some other form of immobilizing bandage. The disadvantage of this is that, as a result of the immobilization, the patient concerned normally cannot use his normal shoes for a longer period of time and is thus correspondingly impeded, and that, in addition, the entire ankle joint is, as a rule, immobilized, which makes extensive physiotherapeutic exercises necessary after the injury has healed. In addition, these rigid bandages have the disadvantage that they can only be used to treat injuries which have already arisen, but as a result of their rigid design cannot be used as a precaution against such injuries.

A bandage for the fixation of the ankle joint is known from DE 43 01 145 A1, that includes a holding bandage which surrounds the middle foot region and a tension strap connected to this holding bandage at the outer side of the foot and extending at least substantially in the direction of the lateral malleolus. In this arrangement the tension strap can be tensioned by means of a ring bandage which surrounds the ankle region and which acts at the end of the tension strap. Through this bandage a situation is achieved in which the outer edge of the foot can be fixed in a slightly raised position, whereby the damaged ligament is relieved, but with the flexibility of the ankle joint in the remaining directions simultaneously being maintained, in particular in the important forward direction.

There are, however, problems with the bandage of DE 43 01 145 A1 in that the holding bandage which spans the middle foot region, and thus also the tension strap which is connected to the holding bandage, cannot be positionally fixed to the foot in all cases. Thus, the holding bandage can, for example, rotate around the middle foot, with the end of the tension strap connected to the holding bandage being simultaneously displaced. In this manner the stabilization of the ankle joint brought about by the tensioned tension strap can be rendered ineffective so that the bandage no longer satisfies its function.

SUMMARY OF THE INVENTION

The object of the present invention is to so design a bandage for the fixation of the ankle joint that a reliable stabilization of the ankle joint can be achieved in all cases so that, with an injury which already exists, the damaged ligament is relieved, with the flexibility of the ankle joint in the remaining directions being simultaneously retained. Furthermore, a bandage of this kind is also designed for prophylactic use to avoid injuries.

This object is satisfied, starting from a bandage of the initially named kind, in that each free tension strap end has a fastener section for the attachment to a part fixed relative to the foot.

The object set is advantageously satisfied by a bandage designed in accordance with the invention. The bandage can, in particular, be used both with an already existing injury and also as a prophylactic measure, since the mobility of the ankle joint is exclusively restricted in the desired sideways direction. Furthermore, through the fixation of the tension strap end or ends to a part fixed relative to the foot, such as for example a sole, a part-sole, an inner shoe, a shoe or an overshoe, a position of action is defined which is non-displaceable relative to the foot, so that a bandage once set in the selected position remains reliably fixed.

It is thus important for the invention that at least one tension strap is provided which extends approximately in accordance with the damaged or torn ligament or the ligament to be protected and can be tensioned between two fixed points provided by the attachment point to the part fixed relative to the foot and by the ring bandage. In this manner it is possible to fix the outer edge of the foot in a slightly raised position and thus to relieve the damaged ligament or the ligament to be protected. As all components of the bandage are of flat design, the bandage is also not intrusive, so that a high acceptance can be achieved, in particular also as a prophylactic measure.

For prophylaxis in particular, a support shoe can, for example, be combined with a bandage designed in accordance with the invention. In this manner a low-cut sports shoe can be used with a bandage in accordance with the invention instead of a customary, ankle-high shoe and prevents twisting of the ankle just as well as or better than the ankle-high sports shoe.

In this respect it is advantageous that, on the one hand, the mobility of the ankle joint is greater in a sports shoe with a low shaft than the mobility with an ankle-high sports shoe, so that, after applying the bandage with a low-cut shoe, whereby the mobility is only restricted in the sideways direction, a mobility of the ankle joint is achieved which is on the whole better. Moreover, through the use of a low-cut shoe the weight caused by the shoes can be reduced, which is in particular advantageous for some kinds of sports such as basketball or volleyball.

In a particularly advantageous embodiment the part of the bandage fixed relative to the foot has a sole-like or part sole-like coupling surface which can be loaded by the forefoot and to which the fastener section of each tension strap can be secured in such a way that the length, the tension and/or the force transmitting coupling point of the respective tension strap can be variably adjusted. In this embodiment the part fixed relative to the foot or the bandage of the invention is of a particularly space-saving design, so that when the bandage is applied, the user can use shoes which he already has available.

Because the coupling surface between the part fixed relative to the foot and each tension strap can be loaded by the forefoot, the body weight can be transferred to the coupling surface. Through the loading with the body weight, the connection at the coupling surface proves to be particularly stable against unintentional release, loosening or slippage, which is of great advantage, in particular with releasable connections. The possibility of variably adjusting the length, the tension, the coupling point at which force acts or the tension direction of the tension straps enables an ideal adaptation of the bandage to the requirements of the particular application, for example the nature of the injury. In particular it is possible, for example during the healing process, for the user to set the tension forces and strap lengths in accordance with his own perception of pain.

When the part fixed relative to the foot is made substantially flat, consists of semi-stiff material and/or is anatomically adaptable to the shape of the sole of the foot, yielding or slippage of the part fixed relative to the foot with jolt-like tensioning of the tension strap or straps is particularly effectively prevented. Furthermore, the part fixed relative to the foot can advantageously be formed as an insole and be inserted into an already available shoe of the wearer, optionally after removal of the previously used in-sole. The part fixed relative to the foot can in particular extend over the entire region of the sole of the foot or only over a part region.

It is preferred that the coupling surface of the part fixed relative to the foot be provided with a hook pile and loop connecting member or adhesive bonding member which extends over an areal region for the attachment of the respective fastener section of each tension strap. Accordingly, the respective fastener section of each tension strap can be formed as a hook pile and loop connecting member or adhesive bonding element for the connection to the part fixed relative to the foot. In this case the connection of the tension strap or straps to the part fixed relative to the foot can be releasable and can be made particularly space-saving so that a high wearing comfort is achieved for the bandage of the invention. When the connection member is attached to the lower side of the part fixed relative to the foot, it can hardly be noticed by the user of the bandage.

In a further advantageous embodiment each end of the tension strap remote from the ring bandage is fixedly connected to the part fixed relative to the foot, in particular sewn thereto. The adjustment of the tension at the respective tension strap takes place in this case by a length adjustment of the tension strap or at the tension strap end adjacent to the ring bandage. The respective tension strap is preferably connected to the ring bandage by means of a connection loop, which is in particular adjustable via a hook pile and loop connection.

For supportive fixation to the foot of the part fixed relative to the foot, the latter can have one or more fixing straps, which are secured to the part fixed relative to the foot and extend along the sides of the foot and the upper side of the foot, in particular crossing each other. The foot can thus be received in the part fixed relative to the foot. It is of advantage when the fixing straps are of adjustable length, in particular via a hook pile and loop connection. The respective fastener section of each free tension strap end can be designed both for attachment directly to the part fixed relative to the foot and also for attachment to one of the fixing straps or to the fixing strap.

In a further advantageous embodiment, the part fixed relative to the foot is formed as an inner shoe in which the foot can be received and which fixes the sole-like or part sole-like coupling surface to the foot. The inner shoe can in this respect be designed as an oversock on which or in which an insole is secured. Thus, this embodiment is also advantageously usable with existing shoes of the wearer.

In an alternative design to the above-named embodiments, the part fixed relative to the foot is formed as a shoe or overshoe and has at least one fastening element provided at the outer side of the foot, in particular in the region of the middle foot, for the attachment of the respective tension straps. In this respect the number of attachment elements corresponds to the number of the free tension strap ends. In this embodiment the sense of feeling of the user of the bandage designed in accordance with the invention is not impaired in any way.

An already existing shoe of the user, such as a sports shoe, a shoe or a sandal, can be converted with very simple means for use with the bandage. This can, for example, be achieved if at least one eye to which the respective tension strap end can be secured is fixed to this shoe, for example at the outer side of the foot. When the part fixed relative to the foot is designed as an overshoe, then an existing shoe can likewise be used. The overshoe need not be a complete shoe, but could, for example, be restricted to a sleeve part which pulls over the front portion of the shoe. Finally, a medical shoe especially designed for orthopaedic purposes can be provided with the bandage of the invention.

The fastener element is preferably formed at the outer side of the shoe or of the overshoe. In this way a particularly simple attachment of each free end of the tension strap is possible, as is the simple application of the bandage, for example with the shoe already pulled on. On the other hand, disturbing pressure points directly at the foot are avoided. The fastener element can also basically be formed at the inner side of the shoe or of the overshoe.

The respective fastener section for the connection of the tension strap to the fastener element at the shoe or overshoe can advantageously include a hook pile and loop connecting element, an adhesive bonding connecting element, a button connection element, an interengaging connecting member, or a laced connecting element. Thus, by way of example, an eye can be attached to the shoe or to the overshoe through which the tension strap is drawn, with the free tension strap end subsequently being turned over through about 180° and connected to the section of the tension strap pointing in the direction of the ankle joint. This connection can take place through hook pile and loop connecting elements or other customary connecting member provided on the tension strap. In order to enable tensioning of the tension strap, each tension strap can be made of adjustable length. In particular, the hook pile and loop connecting member provided at the ankle side section of the tension strap end can extend over a greater region so that the free tension strap end turned over through the eye can be fixed in different positions.

With a button connection a plurality of relatively displaced button holes and buttons can be provided, so that an adjustability and thus tensionability of the tension strap can be achieved in this manner. In similar manner the tension strap can be made tensionable with an adhesively bonded connection or an interengaging connection.

With the various possible embodiments of the part fixed relative to the foot the ring bandage can be connected to a single tension strap end while forming a Y-strap connection or can be connected to two free tension strap ends while forming an X-strap connection in order to enable an effective and spatially fixed force transmission. It is possible to connect the ring bandage to the tension strap or straps via a ring element. Each tension strap can be fixedly connected to the ring element or can be connected in an adjustable connection loop, in particular via a hook pile and loop connection.

In accordance with a further, advantageous embodiment of the invention, a further tension strap is provided at the inner side of the foot and can be tensioned by means of the ring bandage, with the free end of the tension strap having a further fastener section for the attachment to a part fixed relative to the foot, in particular to a sole section, to a shoe or to an overshoe. In this manner a situation is achieved in which both a stabilization of the ankle joint towards the outside and also towards the inside can be achieved by the bandage designed in accordance with the invention, with the mobility of the ankle joint in the remaining directions simultaneously remaining largely unhindered, in particular in the important forward direction.

A shoe or overshoe designed in accordance with the invention is characterized by a fastener element for the attachment of a foot bandage, in particular the free tension strap end of a bandage designed in accordance with the invention, to the outer side of the foot, in particular in the region of the middle foot. The possibility of subsequently attaching the fastener element to the shoe or to the overshoe in particular means that existing shoes can be used so that both the comfort of wearing the bandage and also the acceptance of the bandage is increased.

DESCRIPTION OF PREFERRED EMBODIMENTS

Figure 1A:
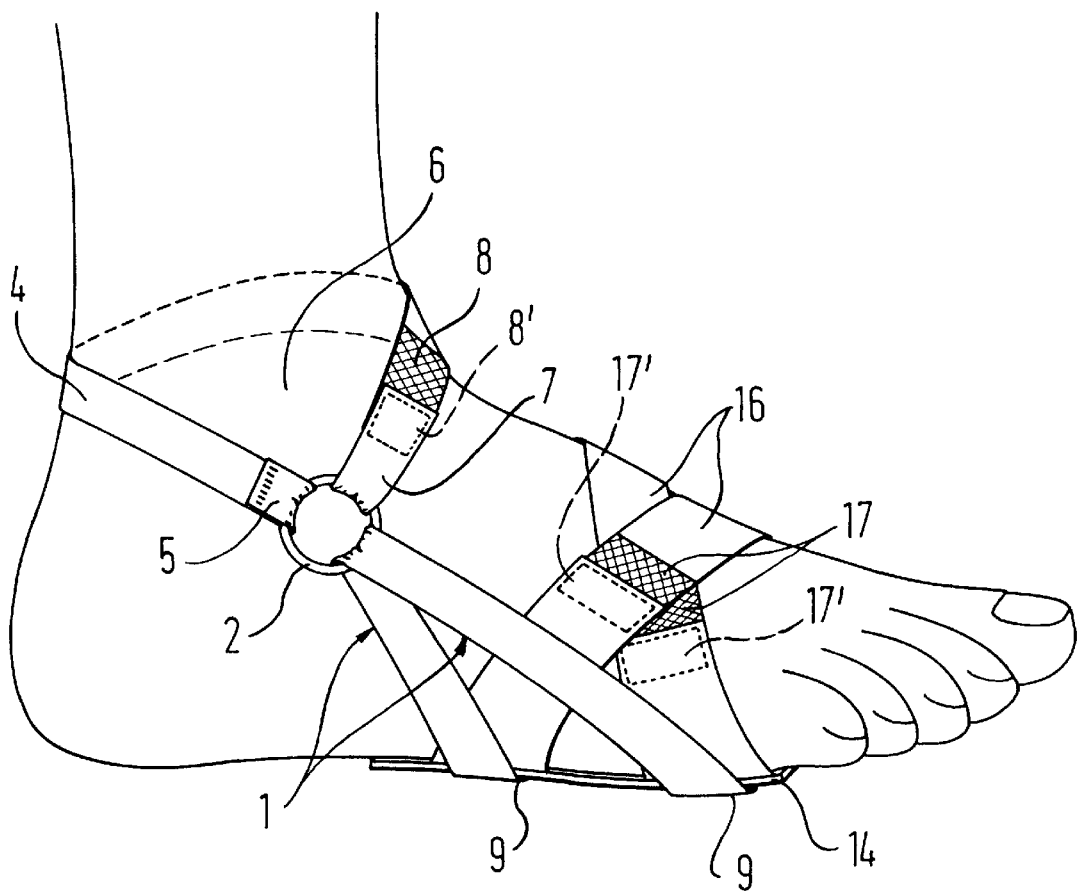
FIG. 1a is a schematic side view of a bandage in accordance with the invention applied to a foot.

FIG. 1a shows a bandage designed in accordance with the invention in the applied state in a schematic view of the outer side of the foot. The bandage has a tension strap 1 which is freely movably looped through a ring 2 located in the ankle region 6. As a consequence of the deflection at the ring 2, a part of the tension strap 1 points in the direction of the outer side edge of the forefoot and the other part of the tension strap 1 points in the direction of the outer side region of the middle foot.

A ring bandage 4 which surrounds the malleolus region 6 is secured to the ring 2. For this purpose one end 5 of the ring bandage 4 is sewn to the ring 2 and thus fixedly connected to the latter. The other end 7 of the ring bandage 4 is looped through the ring 2 and turned over through 180°. The end 7 of the ring bandage has a hook pile and loop connecting element 8' at its non-visible side in FIG. 1a in the region bounded in broken lines which is releasably connected to a hook pile and loop connecting member 8 which extends along the ring bandage 4. The ring bandage 4 can be placed around the malleolus region (ankle region 6) through use of the cooperating hook pile and loop connecting members 8, 8', with it being possible to select different lengths of the ring bandage 4 and/or different positions of the ring 2.

A part 14 fixed relative to the foot contacts the underside of the foot in the region of the forefoot and a part of the metatarsus. The part 14 fixed relative to the foot is flat and is formed of half-stiff deformable material. Its outline corresponds to a section of the outline of the lower side of the foot.

Figure 1B:
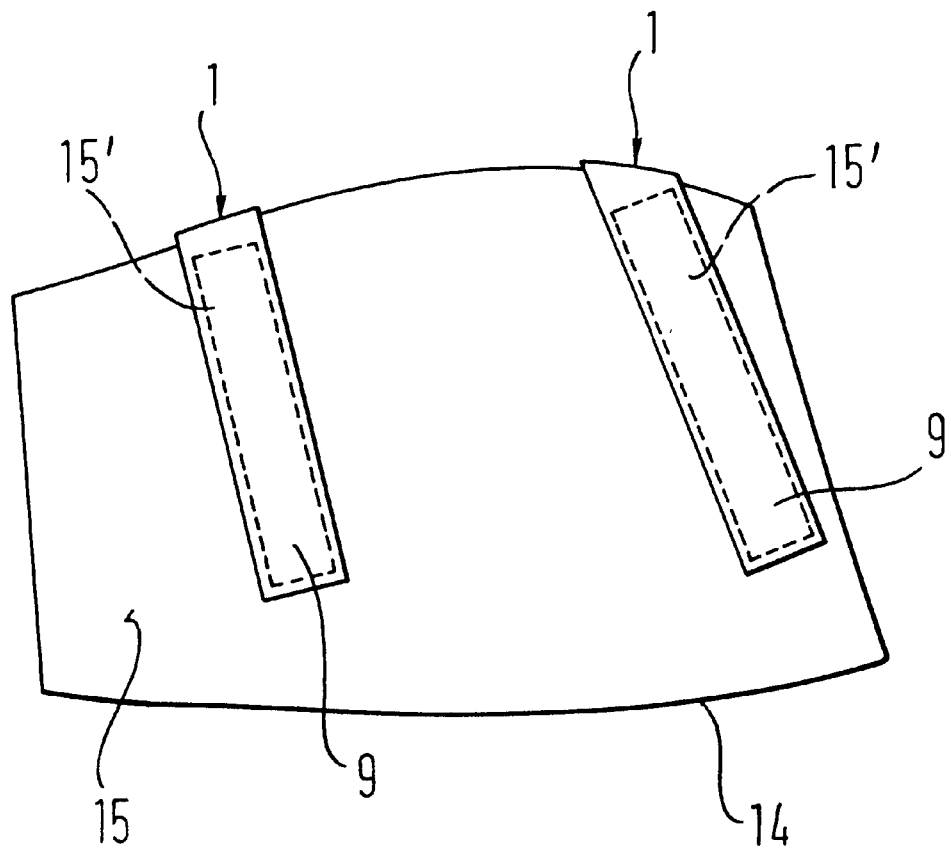
FIG. 1b shows the underside of the part of the bandage of FIG. 1a fixed relative to the foot.

The underside of the part 14 fixed relative to the foot is shown in FIG. 1b, with the outer longitudinal edge being shown in the upper region of FIG. 1b, and the inner longitudinal edge of the part 14 fixed relative to the foot being shown in the lower region. The total lower side of the part 14 fixed relative to the foot as illustrated in FIG. 1b is formed as a coupling surface 15, for example as a hook pile and loop connecting member, for example of the Velcro®-type.

The parts of the tension strap 1 remote from the ring 2 are directed around the longitudinal edge of the part 14 fixed relative to the foot at the outer side of the foot, so that the two tension strap ends 9 extend along the underside of the part 14 fixed relative to the foot. The side of each tension strap end 9 facing the lower side of the foot has a fastener section which is formed as a hook pile and loop connecting member 15' which is releasably connected to the coupling surface 15. The two hook pile and loop connecting members 15' are not visible in FIG. 1b. They are, however, indicated by broken lines.

In each case the ends of two fixing straps 16 are secured to the two longitudinal edges of the upper side of the part 14 fixed relative to the foot, and are, for example, sewn to it. Each fixing strap 16 extends along the outer side of the foot over the upper side of the middle foot to the inner side of the foot. In this arrangement the two fixing straps 16 run cross-wise. The fixing bands 16 are in each case formed of two parts with respective hook pile and loop connecting members 17 and 17' being attached to their confronting ends. The hook pile and loop connecting members 17, 17' cooperate so that the two parts of each fixing strap 15 can be releasably stuck together with variable total lengths.

The bandage in accordance with the invention illustrated in FIGS. 1a and 1b can be applied to the foot by first opening the two hook pile and loop connecting members 8 and 8' of the ring bandage 4, by placing the ring bandage 4 around the ankle region 6 of the foot and connecting the hook pile and loop connecting members 8 and 8' to one another in such a way that the ring bandage 4 closely contacts the ankle region 6. The tension strap 1 can already have been introduced through the ring 2 but is not yet secured to the part 14 fixed relative to the foot.

Thereafter, the middle foot is placed at the upper side of the part 14 fixed relative to the foot, with the fixing straps 16 open, and the respective parts of each fixing straps 16 are connected together by means of the hook pile and loop connecting members 17 and 17', so that the fixing straps 16 tightly surround the middle foot.

Finally, the tension strap 1 is tensioned between the ring bandage 4 and the part 14 fixed relative to the foot in that its two parts remote from the ring 2 are turned around the outer edge of the foot and the two ends 9 of the foot strap 1 are connected to the coupling surface 15.

The bandage has thus been applied to the foot in accordance with the illustration shown in FIG. 1a and tensioned. A sock and/or a normal shoe of the wearer can be placed over the foot bandaged in this way.

On applying the ends 9 of the tension strap 1 to the part 14 fixed relative to the foot, the tension which prevails at the outer side of the foot between the ring bandage 4 and the part 14 fixed relative to the foot can be freely selected. The respective force deflection point of each tension strap end 9 at the outer side of the foot is also individually adjustable. Thus, the bandage of the invention can be individually adapted to the particular conditions of use, such as for example to a prophylactic use or to the position of injured ligaments.

The part 14 fixed relative to the foot is firmly fixed when using the bandage of the invention at the lower side of the foot, because it is tensioned between the lower side of the foot and an applied shoe. The loading transmitted via the lower side of the foot by the body weight prevents the part 14 fixed relative to the foot from slipping, and in particular precisely when a particularly heavy loading of the foot arises with respect to a possible injury or an injury which has already taken place. Furthermore, the shape of the part 14 fixed relative to the foot is adapted to the anatomy of the underside of the foot so that a further stabilization of its position relative to the foot results.

The fixing straps 16 prevent a sliding of the part fixed relative to the foot, in particular in the direction towards the heel of the foot. A design of the part 14 fixed relative to the foot with the fixing straps 16 is thus preferred but not, however, absolutely essential. A slippage of the part 14 fixed relative to the foot in the longitudinal of the foot can, for example, also be prevented in that the part 14 fixed relative to the foot clamped between the lower side of the foot and the applied shoe is formed as an insole, the outline of which corresponds to the total outline of the lower side of the foot. Furthermore, the fixing straps 16 need not be of adjustable length through hook pile and loop connecting members 17, 17', but could also be designed as continuous straps, for example rubber straps. In this case the part 14 fixed relative to the foot is put on the foot by introducing the forefoot into the opening formed by the straps and the part 14 fixed relative to the foot until the straps contact the upper side of the foot and the part 14 fixed relative to the foot lies closely against the lower side of the foot. Because the tension strap 1 is freely movably looped through the ring 2, a total tension can be set which prevails between the ring bandage 4 and the part 14 fixed relative to the foot. In this way a high freedom of movement is achieved with respect to an upward and downward movement of the tip of the foot. It is, however, also possible to connect the tension strap 1 to the ring 2, for example by sewing them together, so that the tension can be set individually between the ring bandage 4 and each of the tension strap ends 9 and their respective coupling points to the part 14 fixed relative to the foot.

The different components of the bandage (in particular the part 14 fixed relative to the foot) can consist, at the side facing the foot) in each case of an adhesive material, so that the bandage is even more stable against slippage at high tensions. In this case it is sensible to first cover the foot with a sock when the bandage has already been applied.

Furthermore, the ring 2 can be made flat to increase the comfort of wearing the bandage. A cushioned cover, which is for example secured to the ring bandage 4, can be provided between the ring 2 and the ankle region 6 of the foot.

Figure 2:
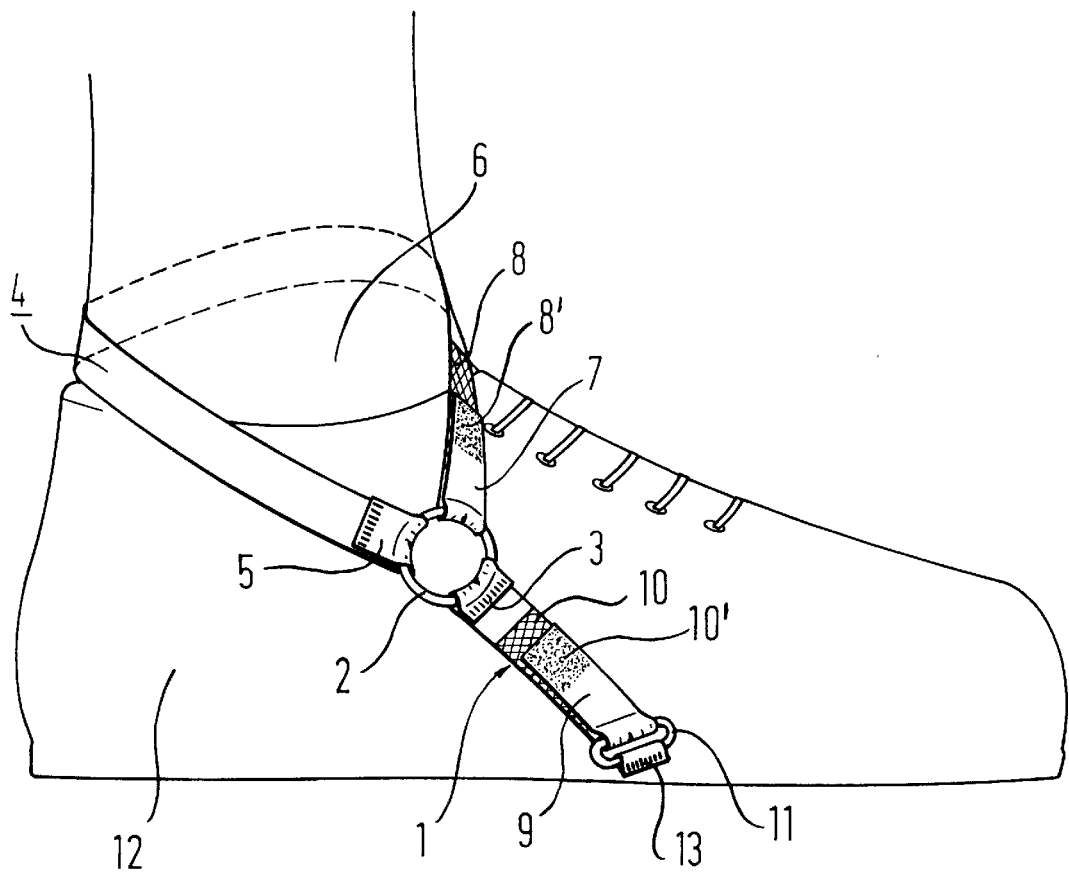
FIG. 2 is a schematic illustration of a further bandage in accordance with the invention in the applied state.

A further bandage designed in accordance with the invention is schematically shown in FIG. 2. This bandage has a tension strap 1, of which the ankle end is secured to a ring 2. The ankle end of the tension strap 1 forms a loop for attachment to the ring 2, with the loop being slung through the ring 2 and secured over the width of the tension strap 1 by stitches 3.

A ring bandage 4 is secured to the ring 2 in the same manner at its one end. The ring bandage 4 passes around the ankle region 6 and is likewise secured to the ring 2 at its other end 7. For this purpose a hook pile and loop connecting member 8 is provided at one side of the ring bandage 4 in the region before its free end 7 and is adhesively connected with a further hook pile and loop connecting member 8' provided in the region of the free end 7, after the free end 7 has been passed through the ring 2 and turned over through about 180°. In order to make this clear, the position of the hook pile and loop connecting member 8' at the rear side of the free end of the ring bandage 4 is shown in FIG. 2 by a grey surface.

Because the hook pile and loop connecting member 8 or the hook pile and loop connecting member 8' cooperating with it extends at the free end 7 of the ring bandage over a larger region of the ring bandage 4, a variable adjustment of the length of the ring bandage 4 is possible, and associated with it a positioning of the ring 2 and also a tensioning of the bandage of the invention, depending on the length of the turned over end of the ring bandage 4.

Basically, the end 5 of the ring bandage 4 can also be made adjustable in similar manner to the free end 7, or only the free end 5 can be made adjustable, while the free end 7 of the ring bandage 4 is fixedly connected to the ring 2, as is shown in the embodiment at the end 5 of the ring bandage. While the tensioning of the ring bandage 4 is possible in simpler manner with a two-sided variable attachment, the one-sided variable attachment has the advantage that the bandage of the invention as a whole consists of parts which are permanently connected together and which cannot be taken apart, so that the danger of losing one element does not exist.

The free end 9 of the tension strap 1 disposed at the sole of the foot is turned over in similar manner to the free end 7 of the ring bandage 4 to form a loop which is held together by a hook pile and loop connecting member 10 provided in the region before the free end and also by a hook pile and loop connecting member 10' provided at the free end 9 of the tension strap 1 and cooperating with the hook pile and loop connecting member 10.

The loop formed by the free end 9 of the tension strap 1 is hung into a ring eye 11, which is connected at the outer side of the foot in the region of the middle foot close to the sole of the shoe 12 to the shoe 12 via a lug 13. Depending on how far the free end 9 of the tension strap 1 is drawn through the ring eye 11 and connected via the two hook pile and loop connecting members 10, 10', a greater or lesser tension of the tension strap 1 is achieved. Through this tension a greater or smaller relief of the lateral ankle joint ligaments, in particular of the ligament extending between the fibula and the talus is possible. Through the bandage of the invention a situation is thus achieved in which the respective ligaments or the respective ligament are or is relieved, and accordingly practically no tension forces can act on this ligament, because the outer edge of the foot is fixed at least in a slightly raised position. An angling of the lower leg to the front and also an angling of the ankle joint to the front or to the rear is not hindered thereby, so that both walking and also an extensive mobility of the ankle joint remain possible with the bandage applied.

Through the coupling of the free end 9 of the tension strap to a fastener element directly at the shoe 12, a positional fixation of the lower point of action of the bandage relative to the foot is achieved so that a bandage in accordance with the invention, after having been set once, does not change its set tension while being worn. In particular it is ensured that with a high loading of the bandage, such as can, for example, occur with a sudden lateral turning over of the foot, no displacement of the points of action of the bandage can occur, so that the bandage reliably remains in the adjusted state.

If a fixation is also desired at the inner side of the foot, in addition to the fixation at the outer side of the foot, for the protection of the ligaments at the inner side of the foot, then a corresponding fastener element can also be provided at the side of the shoe disposed at the inner side of the foot, for example in the form of a ring eye. A further tension strap can then be secured in this ring eye in correspondence with the illustrated embodiment and is connected to the ring bandage 4 via a further connection element disposed at the inner side of the foot, for example in the form of a further ring. The mobility of the ankle joint in the remaining directions, in particular to the front and to the rear, is also preserved in this two-sided embodiment.

In place of the attachment directly to a shoe or to an overshoe, the free end of the tension strap can also be secured to a retaining bandage, which directly surrounds the forefoot or middle foot. The material of this holding bandage is advantageously selected in such a way that a slippage free connection arises between the retaining bandage and the skin of the foot. Through the choice of a suitable material, for example a type of plastic foil, a bonding effect can be achieved which ensures a clear fixation of the coupling point of the tension strap. The material used is preferably so designed that it follows the shape of the foot in order to achieve an adequate resistance against slippage.

The width of the holding bandage should be selected such that, on the one hand, the required area is present between the holding bandage and the surface of the foot to ensure an adequate bonding effect, with an adequate width also avoiding the holding bandage's cutting into the foot. At the same time, the holding strap may not be made so wide that a restriction arises in the wearing comfort or the mobility of the middle foot or forefoot. Advantageous widths lie, for example, in the range between 1 and 8 cm.

It should be noted that the expression "hook pile and loop connecting member" as used throughout this specification is a synonym for the German term "Klettverschluβ", for which there is no correct English language translation, but which is generally understood to be a connection of the Velcro®-type.

A Velcro fastener comprises a first member with a hook pile which cooperates with a second member having a loop pile. On pressing the two members together, the hooks of the hook pile engage in the loops of the loop pile and firmly connect the two members together. Thus, the term "hook pile and loop connecting member" as used in this specification and claims will be understood to specifically mean either a member having a hook pile or a member having a loop pile, and more generally to include a fastener member of the "Velcro"-type or any equivalent fastener design permitting two surfaces to stick together when pressed together but released and restuck many times.

I claim:

1. A bandage for the fixation of an ankle joint of an ankle of a foot, the bandage comprising:
   a ring element positionable in an area of a lateral malleolus; at least one tension strap provided to be placed at an outer side of the foot and connected with the ring element in the area of the lateral malleolus, the at least one tension strap extending from the ring element to at least one free tension strap end, the at least one free tension strap end including a fastener section for fastening to a coupling surface of a part which is to be fixed relative to the foot, the part being configured to be disposed in a region of a middle foot and a forefoot of the foot such that each of the at least one tension strap extends from the ring element substantially in a direction of the middle foot or the forefoot of the foot to the at least one free tension strap end; and a ring bandage positionable to surround a malleolar region of the ankle, the ring bandage having first and second ends arranged to extend substantially in the direction of the lateral malleolus, the first and second ends being connected with the ring element, the ring bandage having a length which is adjustable for tensioning the at least one tension strap.

2. The bandage in accordance with claim 1 wherein the part has a sole-like or part sole-like coupling surface which can be loaded by the forefoot and to which the fastener section of the at least one tension strap can be secured in such a way that a length of the tension strap can be variably adjusted.

3. The bandage in accordance with claim 1 wherein the part has a sole-like or part sole-like coupling surface which can be loaded by the forefoot and to which the fastener section of the at least one tension strap can be secured in such a way that a tension or point of action of the tension strap can be variably adjusted.

4. The bandage in accordance with claim 1 wherein the part is substantially flat and includes a semi-stiff material.

5. The bandage in accordance with claim 1 wherein the part is adaptable to a foot sole shape.

6. The bandage in accordance with claim 1 wherein the coupling surface of the part has a hook pile and loop connecting member or an adhesive bonding member in an areal region.

7. The bandage in accordance with claim 6 wherein the areal region is disposed in a lower side of the part fixed relative to the foot.

8. The bandage in accordance with claim 1 wherein the fastener section of the at least one tension strap includes a hook pile and loop connecting member or an adhesive bonding member for fastening to the coupling surface of the part.

9. The bandage in accordance with claim 1 wherein the part is attachable to the foot by one or more fixing straps which are secured to the part and extend between sides of the foot over an upper side of the foot, each fixing strap being adjustable in length.

10. The bandage in accordance with claim 9 wherein each fixing strap is adjustable in length by a hook pile and loop connection.

11. The bandage in accordance with claim 9 including more than one fixing strap, wherein the fixing straps extend in a cross-wise manner relative to each other.

12. The bandage in accordance with claim 1 wherein the part is formed as an inner shoe for receiving the foot and fixing a sole-like or part sole-like coupling surface to the foot.

13. The bandage in accordance with claim 1 wherein the part is formed as a shoe or overshoe and has at least one fastener element at the outer side of the foot for attachment with the at least one tension strap, the number of the at least one fastener element corresponding to a number of the at least one tension strap end.

14. The bandage in accordance with claim 13 wherein the at least one fastener element is disposed in a region of the middle foot.

15. The bandage in accordance with claim 13 wherein each fastener element is provided at an outer side or an inner side of the shoe or overshoe.

16. The bandage in accordance with claim 13 wherein each fastener element is provided at a region close to a lower side of the shoe or overshoe.

17. The bandage in accordance with claim 13 wherein each fastener element is formed as an eye, a hook pile and loop connecting member, an adhesive bonding member, a press button, a button hole, a band, a hook-shaped member, or a button-shaped member.

18. The bandage in accordance with claim 1 wherein the part is formed as a shoe and the fastener section of the at least one tension strap includes, for connecting to the shoe, a hook pile and loop connecting member, an adhesive bonding connecting member, a button element, a hooking element, or a laced connection element.

19. The bandage in accordance with claim 1 wherein the at least one tension strap is connected with the ring element via a connection loop.

20. The bandage in accordance with claim 19 wherein the connection loop is adjustable via a hook pile and loop connection.

21. The bandage in accordance with claim 1 wherein the ring bandage is fixedly connected to the at least one tension strap.

22. The bandage in accordance with claim 21 wherein the ring bandage is sewn to or formed integrally with the at least one tension strap.

23. The bandage in accordance with claim 21 wherein the ring bandage is connected to the at least one tension strap forming a Y-strap connection or an X-strap connection.

24. The bandage in accordance with claim 21 wherein the ring bandage includes two bands fixed to the at least one tension strap, the two bands connected via hook pile and loop connection members.

25. The bandage in accordance with claim 24 wherein the ring bandage is of a cushion design or broadened at a rear side at least over a portion of a periphery thereof.

26. The bandage in accordance with claim 1 wherein the ring bandage is arranged to form a single loop around the malleolar region of the ankle between the first end and the second end, the first end of the ring bandage being fixedly connected with the ring element, the second end of the ring bandage being adjustably connected with the ring element.

* * * * *